US010472325B2

United States Patent
Mossotti et al.

(10) Patent No.: US 10,472,325 B2
(45) Date of Patent: Nov. 12, 2019

(54) PROCESS FOR THE SYNTHESIS OF PIRFENIDONE

(71) Applicant: PROCOS S.p.A., Cameri (IT)

(72) Inventors: Matteo Mossotti, Carpignano Sesia (IT); Alessandro Barozza, Nosate (IT); Jacopo Roletto, Turin (IT); Paolo Paissoni, Druento (IT)

(73) Assignee: PROCOS S.p.A., Cameri (no) (IT)

( * ) Notice: Subject to any disclaimer, the term of this patent is extended or adjusted under 35 U.S.C. 154(b) by 0 days.

(21) Appl. No.: 15/771,050

(22) PCT Filed: Oct. 27, 2016

(86) PCT No.: PCT/EP2016/075899
§ 371 (c)(1),
(2) Date: Apr. 25, 2018

(87) PCT Pub. No.: WO2017/072216
PCT Pub. Date: May 4, 2017

(65) Prior Publication Data
US 2018/0319747 A1 Nov. 8, 2018

(30) Foreign Application Priority Data
Oct. 29, 2015 (IT) .................. 102015000067092

(51) Int. Cl.
C07D 213/64 (2006.01)

(52) U.S. Cl.
CPC .................. C07D 213/64 (2013.01)

(58) Field of Classification Search
None
See application file for complete search history.

(56) References Cited

U.S. PATENT DOCUMENTS 3,839,346 A  10/1974 Gadekar

FOREIGN PATENT DOCUMENTS

| CN | 1386737 A | 12/2002 |
|---|---|---|
| CN | 1817862 A | 8/2006 |
| CN | 101891676 A | 11/2010 |
| CN | 102558040 A | 7/2012 |
| DE | 2362958 A1 | 6/1974 |
| GB | 1458048 A | 12/1976 |
| WO | WO 03/014087 A1 | 2/2003 |
| WO | WO 2008147170 A1 | 12/2008 |
| WO | WO 2009/035598 A1 | 3/2009 |
| WO | WO 2010/141600 A2 | 12/2010 |

OTHER PUBLICATIONS

Artis Klapars et al; "A General and Efficient Copper Catalyst for the Amidation of Aryl Halides amd the N-Arylation of Nitrogen Heterocycles", Journal of the American Chemical Society, vol. 123, Dec. 7, 2001, pp. 7727-7729.
Internation Search Report and Written Opinion issued in International Application No. PCT/EP2016/075899 dated Feb. 2, 2017.

Primary Examiner — Zinna Northington Davis
(74) Attorney, Agent, or Firm — Arent Fox LLP

(57) ABSTRACT

Disclosed is a process for the synthesis of Pirfenidone (1) from 5-methyl-2(1H)-pyridinone and chlorobenzene in the presence of a catalytic system consisting of a copper salt and an organic ligand, in the presence of a base.

(1)

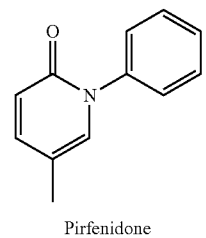

Pirfenidone

The process exploits the high efficiency of the catalytic system consisting of copper(I) salt and an organic ligand in the presence of an inorganic base in the N-amidation reaction of chlorobenzene, a cheap reagent also usable as solvent in this case; reaction conditions at high temperatures, at atmosphere pressure or higher, produce a reaction with good yields.

13 Claims, No Drawings

PROCESS FOR THE SYNTHESIS OF PIRFENIDONE

CROSS-REFERENCE TO RELATED APPLICATION

This application is a 35 U.S.C. 371 National Phase of POT Application No. PCT/EP2016/075899 filed Oct. 27, 2016 which claims priority to IT Application No. 102015000067092 filed Oct. 29, 2015. The disclosure of these prior applications are hereby incorporated by reference herein.

FIELD OF THE INVENTION

The invention relates to a process for the synthesis of Pirfenidone comprising arylation of 5-methyl-2(1H)-pyridinone with chlorobenzene in the presence of a base and in the presence of a catalytic system consisting of a copper (I) salt and an organic ligand.

BACKGROUND OF THE INVENTION

Pirfenidone, 5-methyl-1-phenyl-2(1H)-pyridinone, is a medicament for the treatment of idiopathic pulmonary fibrosis. It has antifibrotic and anti-inflammatory activities, preventing collagen production and fibroblast proliferation.

The literature describes numerous examples of Pirfenidone (1) synthesis starting with 2-amino-5-methylpyridine (2), the diazonium salt and subsequent carbonyl function of which are formed by one-pot synthesis to give the intermediate 5-methylpyridine-2(1H)-one (3). Subsequent arylation of the resulting intermediate leads to the formation of the compound of interest.

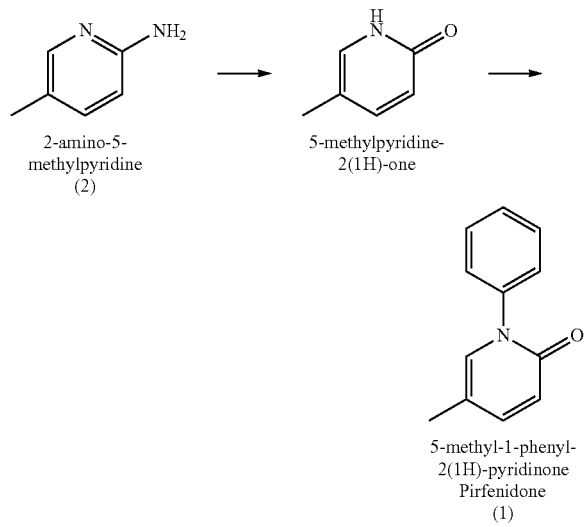

2-amino-5-methylpyridine (2)

5-methylpyridine-2(1H)-one (3)

5-methyl-1-phenyl-2(1H)-pyridinone Pirfenidone (1)

Patent DE2362958 discloses the second step in the synthesis of Pirfenidone (Example 1) from intermediate (3); the operating conditions involve the absence of solvent, the reflux temperature of iodobenzene, and the presence of copper powder and an inorganic base.

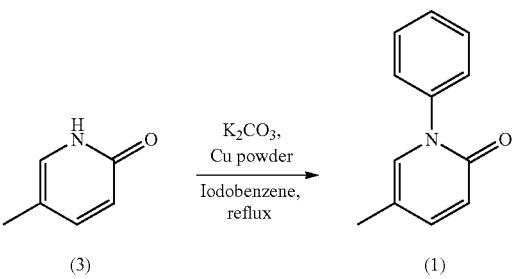

The purification involves decolourising with charcoal, followed by trituration in petroleum ether and subsequent crystallisation in water.

Patent WO2008147170 discloses the reaction of (3) and iodobenzene in the absence of solvent, mediated by copper powder in the presence of potassium carbonate and at the reflux temperature of iodobenzene.

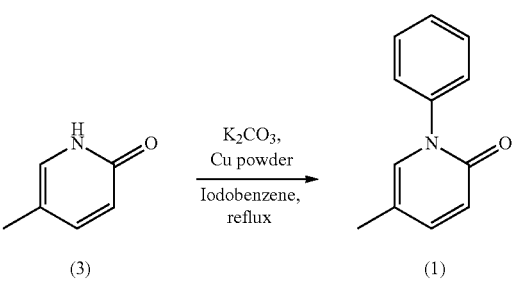

The reaction is followed by an extraction process, treatment with charcoal, and crystallisation.

CN102558040 describes three examples (Examples 1, 2, 3) wherein pyridone intermediate (3) reacts with iodobenzene at its reflux temperature, in the presence of metallic copper and potassium carbonate, in the absence of solvent.

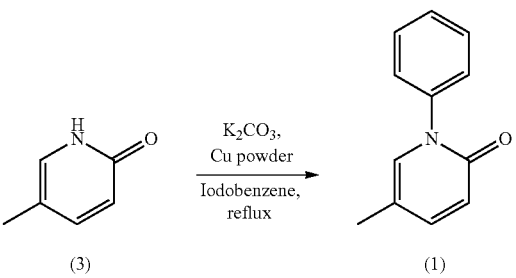

At the end of the reaction the iodobenzene is distilled, followed by a first crystallisation in ethyl acetate, a decolourising treatment with activated charcoal, and subsequent crystallisation from a water/ethanol mixture.

In patent CN1817862 (Example b), intermediate (3) is reacted with iodobenzene under reflux, in the absence of solvent and in the presence of potassium carbonate, but in this case the reaction is catalysed by CuCl.

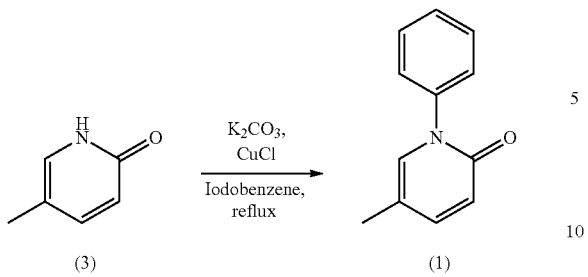

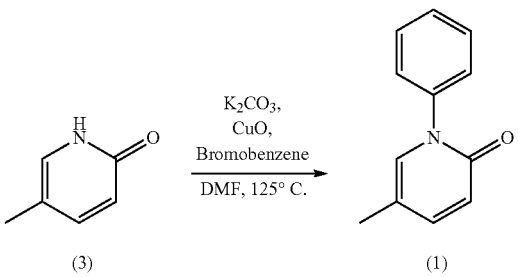

At the end of the reaction an extraction process and acid/base crystallisation are performed.

WO2003014087 (Examples 1, 2, 3 and 4 and reference example) reports the synthesis of (1) by reacting intermediate (3) with bromobenzene at high temperatures in the presence of potassium carbonate and cuprous oxide.

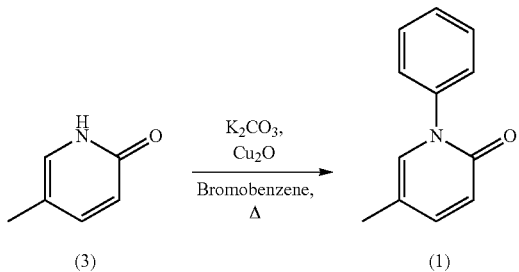

The purification involves an extraction process, a charcoal treatment and acid/base crystallisation.

In patent CN101891676 the reaction between (3) and bromobenzene is always conducted in the absence of solvent, at the reflux temperature of bromobenzene, in the presence of potassium carbonate, but mediated by CuBr.

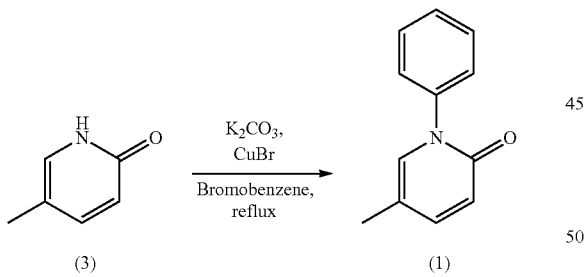

This is followed by distillation of the excess reagent, treatment with charcoal in an aqueous medium, and acid/base crystallisation.

CN1386737 refers to the arylation reaction with various mono-halo-benzene compounds, but does not cite any examples describing that synthetic step.

Patent WO2010141600 describes the synthesis of Pirfenidone (1) which, unlike the process described in the above-mentioned patents, is effected in the presence of a high-boiling solvent (DMF); the reaction is conducted with bromobenzene, claimed by the inventors as being characterised by a dibromobenzene content of less than 0.15% molar or weight/weight, cuprous oxide and potassium carbonate in an inert environment at 125° C.

When the reaction is complete, an extraction process, a charcoal treatment, a first crystallisation in a mixture of organic solvents and a second acid/base crystallisation are effected.

Some articles and patents present in the literature (such as DE2362958, CN1817862 and WO2003014087) mention chlorobenzene as a possible raw material in the synthesis of pirfenidone, but none of them describe the operating conditions with practical examples.

The use of chlorobenzene for the production of Pirfenidone is very interesting from the industrial standpoint as the price of chlorobenzene is far more advantageous than that of bromobenzene, and even more advantageous than that of iodobenzene.

On the basis of this advantage it has surprisingly been discovered that chlorobenzene can be used to synthesise Pirfenidone in industrial reactors which can operate not only at high pressures but also at atmosphere pressure.

DESCRIPTION OF THE INVENTION

The object of the present invention is a process for the synthesis of Pirfenidone (1) comprising arylation of 5-methyl-2(1H)-pyridinone (3) with chlorobenzene in the presence of an inorganic base, at a temperature ranging between 80° C. and 200° C., characterised in that said arylation is conducted in an inert gas atmosphere pressione in the presence of a catalytic system consisting of a copper(I) salt and an organic ligand selected from a compound of formula (4)

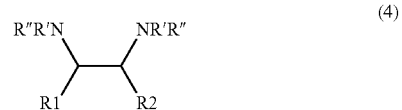

wherein: 0
R1 and R2 are independently hydrogen or a straight or branched $C_{1-7}$ alkyl group; or R1 and R2, taken together with the carbon atoms to which they are bonded, form a 3-7 membered carbocyclic ring;
R' e R" are independently hydrogen or a straight or branched $C_{1-7}$ alkyl group.

DETAILED DESCRIPTION OF THE INVENTION

The arylation of 5-methyl-2(1H)-pyridinone with chlorobenzene can be carried out at atmosphere pressure, for example in an open reactor, or at a pressure exceeding atmosphere pressure, for example in an autoclave.

The reaction can be conducted in the presence or absence of a high-boiling organic solvent.

When optionally present, the organic solvent is selected from dimethylformamide, dimethylsulphoxide, toluene, dioxane and chlorobenzene.

The process is conducted in the presence of an inorganic base, preferably selected from alkali metal hydroxides, carbonates and phosphates, such as sodium carbonate, potassium carbonate, caesium carbonate, lithium carbonate, potassium phosphate, sodium bicarbonate, potassium bicarbonate, sodium hydroxide and potassium hydroxide.

The catalytic system consists of a copper salt system, preferably a copper(I) salt such as copper(I) chloride, copper (I) bromide or copper(I) iodide, combined with an organic ligand of formula (4), such as N,N'-dimethylethylene-1,2-diamine (DMEDA), cyclohexane-1,2-diamine (CHDA), ethylene-1,2-diamine (EDA), N,N'-dimethylcyclohexane-1,2-diamine (DMCDA) and N,N,N',N'-tetramethylethylene-1,2-diamine (TMEDA).

An optimised version of the process of the invention is carried out as follows. The order in which the raw materials are added may differ from that reported below.

Typically, 1 mole of 5-methyl-2(1H)-pyridinone (3) is reacted with 1-50 moles of chlorobenzene, preferably 1.2-10 moles, in the presence of an inorganic base, preferably potassium carbonate, in amounts ranging between 0.5 and 8.0 moles, preferably between 1.0 and 3.0 mole equivalents.

The reaction is carried out in the presence of a copper(I) salt, preferably copper(I) iodide, in amounts ranging between 0.005 and 1 molar equivalent, preferably between 0.01 and 0.5 molar equivalents; the organic ligand, preferably DMEDA, is used in amounts ranging between 0.01 and 2 molar equivalents, preferably between 0.02 and 1 molar equivalent.

The reaction is carried out at temperature range between 80 and 200° C.

When the reaction is conducted at atmosphere pressure, it is performed at a temperature ranging between 100 and 170° C., preferably under reflux.

When the reaction is carried out under pressure, for example in the autoclave, it is performed at a temperature ranging between 120 and 190° C., preferably between 160 and 180° C.

The reaction is carried out in an inert environment, preferably in a nitrogen or argon atmosphere.

The reaction is monitored by UPLC analysis using an ACQUITY UPLC® BEH C18 column, 1.7 µm, 2.1×50 mm, and a water/acetonitrile/0.1% formic acid mixture as the eluent.

After completion of the reaction, the reaction mixture containing Pirfenidone (1) is cooled to 0° C.-40° C., preferably 15° C.-25° C., diluted with an organic solvent, preferably dichloromethane, and filtered. The solution is washed with acid solutions, saline, and water, then concentrated to a residue, under vacuum, at a temperature ranging between 25° C. and 90° C., preferably at 60° C.-70° C., and the resulting solid is purified by crystallisation from organic solvents, typically selected from petroleum ether, heptane, hexane, cyclohexane, pentane, toluene, benzene, ethyl acetate, isopropyl acetate, dichloromethane, isopropyl ether, ethyl ether, methyl-tertbutyl-ether, butanone, acetone, or mixtures thereof in different ratios, typically benzene/petroleum ether, benzene/heptane, benzene/hexane, benzene/cyclohexane, benzene/dichloromethane, benzene/ethyl ether, benzene/isopropyl ether, benzene/methyl-tertbutyl-ether, benzene/isopropyl acetate, benzene/ethyl acetate, benzene/acetone, toluene/petroleum ether, toluene/heptane, toluene/hexane, toluene/cyclohexane, toluene/dichloromethane, toluene/ethyl ether, toluene/isopropyl ether, toluene/methyl-tertbutyl-ether, toluene/isopropyl acetate, toluene/ethyl acetate and toluene/acetone mixtures; if necessary, the resulting solid can be further purified by recrystallisation from solvents, typically selected from water, basic water, methanol, ethanol, acetic acid, isopropanol, acetone, butanone, tetrahydrofuran, acetonitrile, dioxane or mixtures thereof in different proportions, typically water/methanol, water/ethanol, water/acetic acid, water/butanone, water/acetone, water/acetonitrile and water/tetrahydrofuran mixtures.

Finally, the mixture is dried under vacuum at the temperature of 30° C.-90° C., preferably at 45° C.-55° C., to obtain Pirfenidone with a purity exceeding 98%.

The process according to the invention is advantageous as chlorobenzene is a more readily available and cheaper reagent than other mono-halobenzene compounds, and easily removable during the final product purification steps.

The invention will now be illustrated in detail by the following examples.

EXAMPLES

Example 1: Synthesis of Pirfenidone (1)

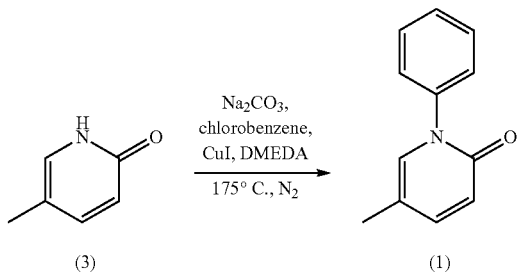

N,N'-Dimethylethylene-1,2-diamine (8.4 g, 95.3 mmol) and CuI (9.08 g, 47.65 mmol) are added to a suspension of 5-methyl-2(1H)-pyridinone (3) (20 g, 183.26 mmol) and sodium carbonate (40.96 g, 386.46 mmol) in chlorobenzene (100 mL), stirred in the autoclave. The autoclave is hermetically sealed, and the reaction medium is rendered inert with vacuum/$N_2$ cycles. The mixture is heated to 175° C. under magnetic stirring for 19 hours. After completion of the reaction, the mixture is cooled to 25° C. and diluted with ethyl acetate. The resulting mixture is washed 4 times with 2N HCl, 3 times with a saturated $NH_4Cl$ solution, and twice with water. The organic phase is dried and concentrated to a residue. The resulting product is dissolved in ethyl acetate, and hexane is added to the resulting solution; the mixture is left to cool slowly to room temperature (RT), and the resulting pale precipitate is stirred for 1 hour at RT and a further hour at 5° C. The suspension is filtered under vacuum, and the resulting solid is washed with hexane and dried; crude Pirfenidone (1), with a purity exceeding 95%, is obtained. The beige solid is dissolved in hot water and stirred, in the presence of activated charcoal, for 1 hour. The charcoal is filtered out and washed with hot water. The resulting solution is slowly cooled to RT, then stirred at that temperature for 1 hour and cooled to 5° C., stirring for 1 hour. The resulting pale solid is filtered under vacuum, washed with cold water, and dried. Molar yield from 5-methyl-2(1H)-pyridinone (3) to Pirfenidone (1): 76%.

Example 2: Synthesis of Pirfenidone (1)

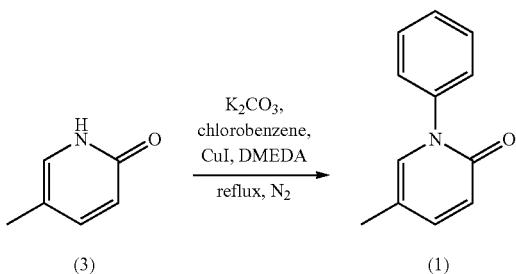

N,N'-Dimethylethylene-1,2-diamine (3.52 g, 39.92 mmol) and CuI (3.8 g, 19.96 mmol) are added to a suspension of 5-methyl-2(1H)-pyridinone (3) (20 g, 183.26 mmol) and potassium carbonate (27.86 g, 201.59 mmol) in chlorobenzene (80 mL). The reaction medium is rendered inert with vacuum/N$_2$ cycles, and the mixture is refluxed, under magnetic stirring, for 16 hours. After completion of the reaction, the mixture is cooled to 25° C. and diluted with dichloromethane, and insolubles are filtered off. The resulting mixture is washed twice with 2N HCl, 3 times with an EDTA aqueous solution, and twice with water. The organic phase is dried and concentrated to a residue. The resulting product is dissolved in hot toluene, and n-heptane is added to the resulting solution; the mixture is slowly cooled to RT and the resulting clear precipitate is stirred for 1 hour at RT and a further hour at 5° C. The suspension is filtered under vacuum, and the resulting solid is washed with n-heptane and dried; crude Pirfenidone (1), with a purity exceeding 95%, is obtained. The beige solid is dissolved in hot butanone, and water is added to the resulting solution; the solution is stirred hot, in the presence of activated charcoal, for 1 hour. The charcoal is filtered off and washed with hot water. The resulting solution is slowly cooled to RT, then stirred at that temperature for 1 hour and cooled to 5° C., stirring for 1 hour. The resulting clear solid is filtered under vacuum, washed with cold water, and dried. Molar yield from 5-methyl-2(1H)-pyridinone (3) to Pirfenidone (1): 84%.

Example 3: Synthesis of Pirfenidone (1)

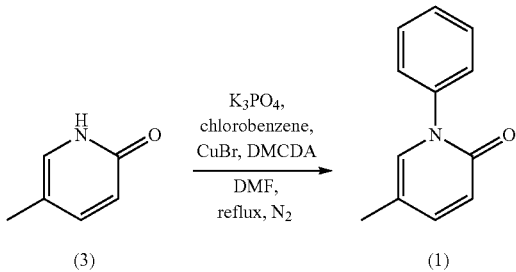

Chlorobenzene (37 mL, 366.52 mmol), N,N'-dimethylcyclohexane-1,2-diamine (6.52 g, 45.82 mmol) and CuBr (3.29 g, 22.91 mmol) are added to a suspension of 5-methyl-2(1H)-pyridinone (3) (20 g, 183.26 mmol) and potassium phosphate (77.8 g, 366.52 mmol) in DMF (80 mL). The reaction medium is rendered inert with vacuum/N$_2$ cycles, and the mixture is refluxed, under magnetic stirring, for 19 hours. After completion of the reaction, the mixture is cooled to 25° C. and diluted with toluene, and insolubles are filtered off. The resulting mixture is washed twice with 2N HCl, 3 times with an EDTA aqueous solution, and twice with water. The organic phase is dried and concentrated to a residue. The resulting product is dissolved in hot toluene, and n-heptane is added to the resulting solution. The mixture is slowly cooled to RT, and the resulting pale precipitate is stirred for 1 hour at RT and a further hour at 5° C. The suspension is filtered under vacuum, and the resulting solid is washed with n-heptane and dried; crude Pirfenidone (1), with a purity exceeding 95%, is obtained. The beige solid is dissolved in hot acetic acid, and activated charcoal is added to the resulting solution, which is stirred hot for 1 hour. The charcoal is filtered off and washed with hot water. The resulting solution is slowly cooled to RT, and a solution of NaOH is added until a basic pH is obtained; the solution is then stirred for 1 hour and cooled to 5° C., stirring for 1 hour. The resulting pale solid is filtered under vacuum, washed with cold water, and dried. Molar yield from 5-methyl-2(1H)-pyridinone (3) to Pirfenidone (1): 80%.

Example 4: Synthesis of Pirfenidone (1)

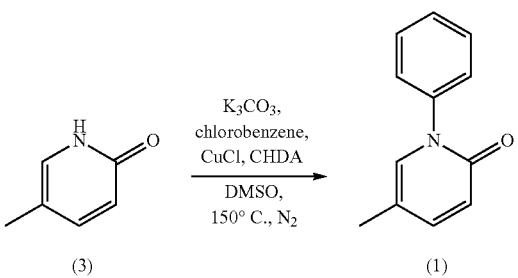

Chlorobenzene (56 mL, 549.78 mmol), cyclohexane-1,2-diamine (8.37 g, 73.32 mmol) and CuCl (3.63 g, 36.66 mmol) are added to a suspension of 5-methyl-2(1H)-pyridinone (3) (20 g, 183.26 mmol) and potassium carbonate (53.41 g, 386.46 mmol) in DMSO (50 mL), stirred in the autoclave. The autoclave is hermetically sealed, and the reaction medium is rendered inert with vacuum/N$_2$ cycles. The mixture is heated to 150° C. under magnetic stirring for 19 hours. After completion of the reaction, the mixture is cooled to 25° C. and diluted with toluene. The resulting solution is washed twice with 2N HCl, 3 times with a saturated solution of NH$_4$Cl, and with water. The organic phase is dried and concentrated to a residue. The resulting product is dissolved hot in benzene, and cyclohexane is added to the resulting solution. The mixture is slowly cooled to RT and the resulting pale precipitate is stirred for 1 hour at RT and a further hour at 5° C. The suspension is filtered under vacuum, and the resulting solid is washed with cyclohexane and dried; crude Pirfenidone (1), with a purity exceeding 95%, is obtained. The beige solid is dissolved hot in methanol, and water is added to the resulting solution; the solution is stirred hot, in the presence of activated charcoal, for 1 hour. The charcoal is filtered off and washed with hot water. The resulting solution is slowly cooled to RT, then stirred at that temperature for 1 hour and cooled to 5° C., stirring for 1 hour. The resulting pale solid is filtered under vacuum, washed with cold water, and dried. Molar yield from 5-methyl-2(1H)-pyridinone (3) to Pirfenidone (1): 75%.

Example 5: Synthesis of Pirfenidone (1)

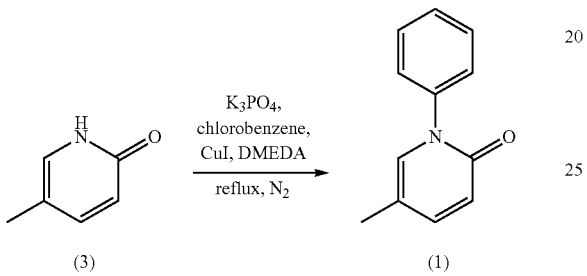

N,N'-Dimethylethylene-1,2-diamine (4.85 g, 54.98 mmol) and CuI (5.24 g, 27.49 mmol) are added to a suspension of 5-methyl-1-phenyl-2(1H)-pyridinone (3) (20 g, 183.26 mmol), potassium phosphate (112.81 g, 531.46 mmol) in chlorobenzene (80 mL), under magnetic stirring. The reaction medium is rendered inert with vacuum/$N_2$ cycles, and the mixture is refluxed, under magnetic stirring, for 19 hours. After completion of the reaction, the mixture is cooled to 25° C. and diluted with toluene. The resulting mixture is washed twice with 2N HCl, 3 times with water, 3 times with an $NH_4Cl$ solution, and twice with water. The organic phase is dried and concentrated to a residue. The resulting product is dissolved in hot toluene, and n-heptane is added to the resulting solution. The mixture is slowly cooled to RT, and the resulting pale precipitate is stirred for 1 hour at RT and a further hour at 5° C. The suspension is filtered under vacuum, and the resulting solid is washed with n-heptane and dried; crude Pirfenidone (1), with a purity exceeding 95%, is obtained. The beige solid is dissolved in hot ethanol, and water is added to the resulting solution; the solution is stirred while hot, in the presence of activated charcoal, for 1 hour. The charcoal is filtered off and washed with hot water. The resulting solution is slowly cooled to RT, then stirred at that temperature for 1 hour and cooled to 5° C., stirring for 1 hour. The resulting pale solid is filtered under vacuum, washed with 2 volumes of cold water, and dried. Molar yield from 5-methyl-2(1H)-pyridinone (3) to Pirfenidone (1): 72%

Pirfenidone (1) obtained from examples 1-4 has the following characteristics:

UPLC-MS [M+H]$^+$=186 m/z $^1$H-NMR (in $CDCl_3$ at 400 MHz): 7.44-7.52 (2H, m), 7.39-7.43 (1H, m), 7.34-7.39 (2H, m), 7.28 (1H, q), 7.13 (1H, m), 6.63 (1H, d), 2.12 (3H, s).

$^{13}$C-NMR (in $CDCl_3$ at 100 MHz): 161.72, 142.54, 141.18, 135.32, 129.28, 128.31, 126.59, 121.50, 114.76, 17.00.

The invention claimed is:
1. A process for the synthesis of Pirfenidone (1)

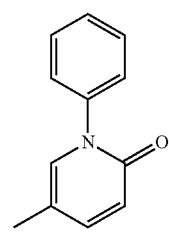

comprising the arylation of 5-methyl-2(1H)-pyridinone (3)

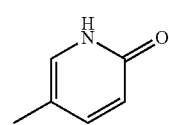

with chlorobenzene in the presence of an inorganic base, at a temperature ranging between 80° C. and 200° C., wherein, said arylation is carried out in an inert gas atmosphere and in the presence of a catalytic system consisting of a copper salt and an organic ligand selected from a compound of formula (4)

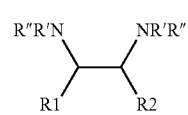

wherein:
R1 and R2 are independently hydrogen or a linear or branched C1-7 alkyl group; or R1 and R2 taken together with the carbon atoms they are linked to form a 3-7 membered carbocyclic ring;
R' and R" are independently hydrogen or a linear or branched C1-7 alkyl group.

2. The process of claim 1, wherein said arylation is carried out at atmospheric pressure at a temperature ranging between 100 and 170° C.

3. The process of claim 1, wherein said arylation is carried out at a pressure higher than atmospheric pressure at a temperature ranging between 120 and 190° C.

4. The process of claim 3, which is performed at a temperature ranging between 160 and 180° C.

5. The process according to claim 1, wherein said arylation is carried out in the absence of solvent.

6. The process according to claim 1, wherein said arylation is carried out in a solvent selected from dimethylformamide, dimethylsulfoxide, toluene, dioxane or chlorobenzene.

7. The process according to claim 1, wherein the inorganic base is selected from alkali metal hydroxides, carbonates and phosphates.

8. The process according to claim 1, wherein the copper salt is selected from copper(I) chloride, copper(I) bromide and copper(I) iodide.

9. The process according to claim 1, wherein the organic ligand of formula (4) is selected from N,N'-dimethylethylene-1,2-diamine, cyclohexane-1,2-diamine, N,N'-dimethylcyclohexane-1,2-diamine, ethylene-1,2-diamine, and N,N,N',N'-tetramethylethylene-1,2-diamine.

10. The process according to claim 1, wherein, for 1 molar equivalent of 5-methyl-2(1H)-pyridinone (3), the copper salt is used in an amount ranging between 0.005 and 1 molar equivalent and the organic ligand is used in an amount ranging between 0.01 and 2 molar equivalents.

11. The process according to claim 7, wherein the inorganic base is potassium carbonate.

12. The process according to claim 8, wherein the copper salt is copper (I) iodide.

13. The process according to claim 10, wherein the copper salt is used in an amount ranging between 0.01 and 0.5 molar equivalent and the organic ligand is used in an amount ranging between 0.02 and 1 molar equivalent.

* * * * *